United States Patent [19]

Manoury et al.

[11] Patent Number: 4,794,120
[45] Date of Patent: Dec. 27, 1988

[54] ANTIPARASITIC NITROFURAN DERIVATIVES

[75] Inventors: Philippe Manoury, Verrieres le Buisson; Jean Binet, Breuillet; Michel Aletru, Paris, all of France

[73] Assignee: Synthelabo, Paris, France

[21] Appl. No.: 70,541

[22] Filed: Jul. 7, 1987

[30] Foreign Application Priority Data

Jul. 8, 1986 [FR] France ............... 86 09886

[51] Int. Cl.⁴ ............... A61K 31/435; A61K 31/345; C07D 471/04; C07D 307/75
[52] U.S. Cl. ............... 514/249; 514/258; 514/299; 514/300; 514/368; 514/394; 514/414; 544/282; 544/350; 546/112; 546/121; 546/183; 548/154; 548/327; 548/453
[58] Field of Search ............... 544/282, 350; 546/112, 546/121, 183; 548/154, 327, 453; 514/249, 258, 299, 300, 368, 394, 414

[56] References Cited

U.S. PATENT DOCUMENTS 3,424,845  1/1969  Berndt et al. ............... 549/482
4,051,253  9/1977  Hein et al. ............... 549/481

Primary Examiner—Mary C. Lee
Assistant Examiner—Bernard A. Dentz
Attorney, Agent, or Firm—Wegner & Bretschneider

[57] ABSTRACT

Nitrofuran derivatives of formula (I)

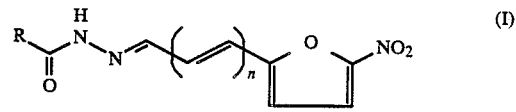

in which n is 0 or 1 and R is a selected heterocyclic radical have useful antibacterial, antiparasitic and antifungal activity.

2 Claims, No Drawings

ANTIPARASITIC NITROFURAN DERIVATIVES

The present invention relates to nitrofuran derivatives, their preparation and to compositions containing them.

According to the invention there are provided nitrofuran derivatives of the formula (I)

in which n is 0 or 1 and R is an imidazo[1,2-a]pyrid-2-yl, imidazo[2,1-b]thiazol-6-yl, imidazo[1,2-a]pyrazin-2-yl, 5,6,7,8-tetrahydroimidazo[1,2-a]pyrazin-2-yl, 7-acetyl-5,6,7,8-tetrahydroimidazo[1,2-a]pyrazin-2-yl, imidazo[1,5-a]pyrid-1-yl, imidazo[1,5-a]pyrid-3-yl, pyrazolo[1,5-a]pyrid-3-yl, 1-indolizinyl, 3-indolizinyl, 5,6,7,8-tetrahydro-1-indolizinyl, 5,6,7,8-tetrahydro-2-indolizinyl, 6H-thieno[2,3-b]pyrrol-5-yl, 4H-thieno[3,2-b]pyrrol-5-yl, 4-oxo-4H-pyrido[1,2-a]pyrimidin-3-yl, benzimidazol-2-yl or imidazo[1,2-a]pyrid-3-yl radical.

The compounds of formula (I) may be prepared by condensing a hydrazide of formula (II)

(wherein R is as herein defined) with 5-nitro-2-furancarbaldehyde or its vinylogue, 3-(5-nitro-2-furyl)-2-propenal. The condensation is suitably effected in an alcohol solvent (such as methanol, ethanol or 2-methoxyethanol) maintained at a temperature from 20° C. to its refluxing temperature. The derivatives obtained crystallize spontaneously in the reaction medium.

3-(5-Nitro-2-furyl)-2-propenal is prepared by an aldolization reaction between 5-nitro-2-furancarbaldehyde and acetaldehyde, followed by a purification by chromatography on a silica column.

The hydrazides (II) may be prepared by reaction between the corresponding acids (RCOOH) or the esters of the corresponding acids described in the literature and dry hydrazine, in the presence or absence of condensing agents (such as, for example, dicyclohexylcarbodiimide or 2-ethoxy-1-ethoxycarbonyl-1,2-dihydroquinoline.

The Examples which follow illustrate the invention.

The structure of the compounds was confirmed by analyses and their IR and NMR spectra.

EXAMPLE 1

Imidazo[1,2-a]pyridine-2-carboxylic acid [(5-nitro-2-furyl)methylene]hydrazide

1.1. Imidazo[1,2-a]pyridine-2-carbohydrazide 4.2 ml of triethylamine are added to a suspension of 8.1 g of ethyl imidazo[1,2-a]-pyridine-2-carboxylate hydrobromide (described by J. G. Lombardino, J. Org. Chem. 30, 2403, 1965) in 75 ml of toluene. After the mixture has been filtered and the toluene evaporated off, the residue is taken up with 75 ml of ethanol and 6 ml of hydrazine and the mixture is then brought to the refluxing temperature for 4 h.

The precipitate is filtered off and imidazo[1,2-a]-pyridine-2-carbohydrazide obtained.

M.p. 195°–198° C.

1.2. Imidazo[1,2-a-]pyridine-2-carboxylic acid [(5-nitro-2-furyl)methylene]hydrazide A suspension of 5.2 g (0.037 mole) of 5-nitro-2-furancarbaldehyde and 6 g (0.034 mole) of the hydrazide obtained above in 150 ml of methanol is brought to the refluxing temperature for 3 h.

After the mixture has cooled, the precipitate is filtered off and taken up with boiling methanol, and the product is filtered off and dried. The compound is obtained.

M.p. 280° C.

EXAMPLE 2

Imidazo[2,1-b]thiazole-6-carboxylic acid [(5-nitro-2-furyl)-2-propen1-ylidene]hydrazide According to the same procedure as in Example 1.2., 1.1 g (0.065 mole) of 3-(5-nitro-2-furyl)-2-propenal and 1.2 g of imidazo[2,1-b]-thiazole-6-carbohydrazide are reacted in methanol. The compound, melting point 332° C., is obtained.

EXAMPLE 3

7-Acetyl-5,6,7,8-tetrahydroimidazo[1,2-a]pyrazine-2-carboxylic acid [(5-nitro-2-furyl)methylene]hydrazide

3.1. 7-Acetyl-5,6,7,8-tetrahydroimidazo[1,2-a]pyrazine-2-carbohydrazide 5.9 g (0.03 mole) of ethyl 5,6,7,8-tetrahydroimidazo[1,2-a]pyrazine-2-carboxylate, described by J. P. Chapat, J. Chem. Research, 1984, 488–80, are added to 8.3 ml of acetic anhydride which has been cooled to 0°–5° C., and the mixture is left for 2 days.

The latter is poured into ice-cold water and extracted with methylene chloride, and the organic phase is then washed with water until the pH is neutral. The organic phase is dried, filtered and evaporated. Ethyl 7-acetyl-5,6,7,8-tetrahydroimidazo[1,2-a]pyrazine-2-carboxylate is obtained.

M.p. 97° C.

6 g of the ester thereby obtained, in 10 ml of hydrazine, are brought to the refluxing temperature for 20 min. The excess hydrazine is evaporated off and the oil obtained purified by chromatography on a silica column (methylene chloride/methanol/ammonia solution 19:10:1).

The hydrazide is obtained.

M.p. 182° C.

3.2. 7-Acetyl-5,6,7,8-tetrahydroimidazo[1,2,-a]pyrazine-2-carboxylic acid [(5-nitro-2-furyl)methylene]hydrazide According to the same procedure as in Example 1.2., 1.9 g of the hydrazide obtained above and 1.3 g of 5-nitro-2-furancarbaldehyde are reacted in methanol. The compound, melting point 255° C., is obtained.

EXAMPLE 4

3-Phenylimidazo[1,2-a]pyridine-2-carboxylic acid[(5-nitro-2-furyl)methylene]hydrazide

4.1. Ethyl 3-bromo-3-phenyl-2-oxopropionate 39.3 g (0.08 mole) of pyrrolidone hydrotribromide (PHT) are introduced portionwise at approximately 10° C. into a solution of 13.9 g (0.072 mole) of ethyl 2-oxo-3-phenylpropanoate (described by E. L. Eliel et al. J. Org. Chem. 37, 505, 1972) in 250 ml of tetrahydrofuran (THF) and 6.1 g (0.072 mole) of 2-pyrrolidone. The temperature of the mixture is allowed to return to 20° C. and the mixture is then heated to 50° C. for 1 h. The mixture is cooled and then poured onto ice. The mixture is extracted with ether and the organic phase washed with water, dried with MgSO$_4$, filtered and evaporated. 18 g of oil are obtained, which is used in the crude state for the next stage of the reaction.

4.2. Ethyl 3-phenylimidazo[1,2-a]pyridine-2-carboxylate 19.5 g (0.07 mole) of the above oil, dissolved in 70 ml of dimethoxyethane, are added slowly at room temperature to a solution of 13.4 g (0.143 mole) of 2-aminopyridine in 100 ml of dimethoxyethane. When the addition is complete, the mixture is heated to 80°–90° C. for 2 h and then evaporated. The evaporation residue is taken up with water and extracted with methylene chloride, and the extract is dried with MgSO$_4$, filtered and evaporated. The crude product is purified by chromatography on a silica column (eluent: CH$_2$Cl$_2$/CH$_3$OH 95:5).

6.2 g of ethyl 3-phenylimidazo[1,2-a]pyridine-2-carboxylate are obtained.

M.p. 106° C.

Ethyl 2-phenylimidazo[1,2-a]pyridine-3-carboxylate (m.p. 68° C.) and ethyl 2-(4-hydroxyphenyl)imidazo[1,2-a]pyridine-3-carboxylate (m.p. 220° C.) are obtained in the same way.

4.3. 3-Phenylimidazo[1,2-a]pyridine-2-carbohydrazide

The hydrazide is prepared as described in Example 1.1., by reacting 5.6 g (0.02 mole) of the above ester with 4 ml of anhydrous hydrazine in 150 ml of ethanol. The compound, melting point 233° C., is obtained.

4.4. 3-Phenylimidazo[1,2-a]pyridine-2-carboxylic acid [(5-nitro-2-furyl)methylene]hydrazide Using the procedure described in 1.2., 2.5 g (0.01 mole) of the above hydrazide and 1.6 g (0.011 mole) of 5-nitro-2-furancarbaldehyde are reacted in 100 ml of methanol.

The product, melting point 245° C., is obtained.

EXAMPLE 5

3-Methylsulphinylimidazo[1,5-a]pyridine-1-carboxylic acid [(5-nitro-2-furyl)methylene]hydrazide

5.1. 3-Methylsulphinyl-1-trifluoroacetylimidazo[1,5-a]pyridine

A solution of 15.6 g (0.06 mole) of 3-methylthio-1-trifluoroacetylimidazo[1,5-a]pyridine (J. Bourdais et al. J. Het. Chem. 17, 1351, 1980) in 750 ml of chloroform is cooled to 5° C. 30.6 g (0.132 mole) of m-chloroperbenzoic acid is added in the course of approximately 1 h.

The mixture is stirred for 1 h 30 min, the precipitate is filtered off and the organic phase is washed with sodium bisulphite solution, then with sodium bicarbonate solution and then with water. The chloroform phase is dried with MgSO$_4$, filtered and evaporated.

The product is purified by chromatography on a silica column. The product, melting point 140° C., is obtained.

5.2. 3-Methylsulphinylimidazo[1,5-a]pyridine-1-carboxylic acid 15.3 g (0.05 mole) of the above product is added portionwise at approximately 5° C. to 200 ml of 87.5% strength ethanol containing 59 g of potassium hydroxide. The mixture is stirred for 20 min after the addition is complete and the precipitate obtained is filtered off.

The latter is taken up in 100 ml of water, the mixture is acidifed to pH 1 with 3N HCl and stirred for 1 h, and the precipitate is filtered off and dried.

The product, melting point 200° C., is obtained.

5.3. 3-Methylsulphinylimidazo[1,5-a]pyridine-1-carbohydrazide 2 ml of Et$_3$N is added to 3 g (0.013 mole) of the above acid dissolved in 100 ml of chloroform.

The solution is cooled to approximately 0° C. and 1.4 ml (0.015 mole) of ethyl chloroformate dissolved in 5 ml of chloroform are added. The solution is stirred for 1 h 30 min at 5° C. and is then added to 130 ml of chloroform containing 4.2 ml of hydrazine.

The temperature is allowed to return to 20° C., the mixture stirred for 1 h 30 min and the precipitate filtered off. The product, melting point 188° C., is thereby obtained.

5.4. 3-Methylsulphinylimidazo[1,5-a]pyridine-1-carboxylic acid [(5-nitro-2-furyl)methylene]hydrazide This product is prepared using the method described in Example 1, starting with 1.5 g of the above hydrazide in 300 ml of methanol and 1 g (0.006 mole) of 5-nitro-2-furancarbaldehyde.

M.p. 294° C.

EXAMPLE 6

Imidazo[1,5-a]pyridine-1-carboxylic acid [(5-nitro-2-furyl)methylene]hydrazide

6.1. Ethyl imidazo[1,5-a]pyridine-1-carboxylate 11.2 g (0.078 mole) of imidazo[1,5-a]pyridine-1-carbonitrile (Y. A. Saednya, Synthesis 1983, 748) in 300 ml of ethanol is brought to reflux for 16 hours while gaseous HCl is bubbled through.

The solution is evaporated to dryness and the residue taken up with water and extracted with ether. The organic phase is washed with water, bicarbonate and water. The product is obtained after evaporation.

M.p. 141° C.

6.2. Imidazo[1,5-a]pyridine-1-carbohydrazide

The procedure described in Example 1 is used, starting with 10.2 g (0.05 mole) of the above ester and 20 ml of hydrazine. The product, melting point 189° C., is obtained.

6.3 Imidazo[1,5-a]pyridine-1-carboxylic acid [(5-nitro-2-furyl)methylene]hydrazide The product is prepared according to Example 1, starting with 1.3 g (0.007 mole) of the above hydrazide and 1.1 g (0.008 mole) of 5-nitro-2-furancarbaldehyde. The product, which melts at 300° C. with decomposition, is obtained.

The hydrazides (II), which are the starting substances, are shown in Table I.

The final compounds (I) prepared by way of example are shown in Table II.

TABLE I
R—CO—NH—NH₂     (II)
| R | M.p. (°C.) | R | M.p. (°C.) |
|---|---|---|---|
| 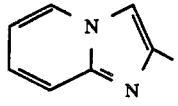 | 195–198 | 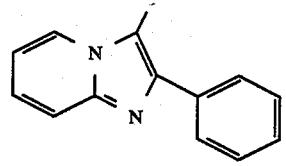 | 142 |
| 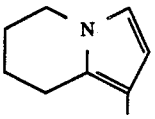 | 237 | 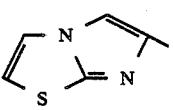 | 127 |
| 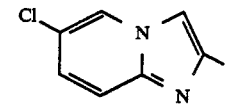 | 207 | 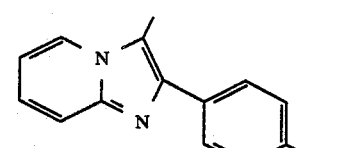 | 269 |
| 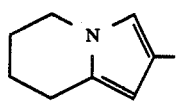 | 233 | 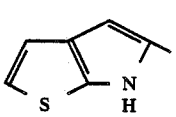 | 179 |
| 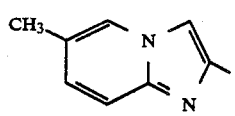 | 224 | 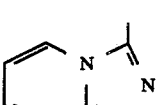 | 182 |
| 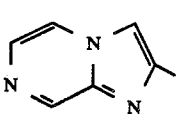 | 192 | 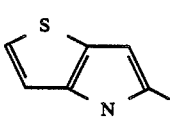 | 230 |
| 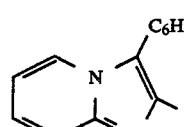 | 258 | 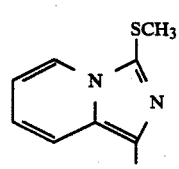 | 234 |
| 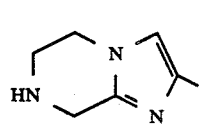 | 159 | 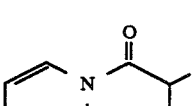 | 270 |
| 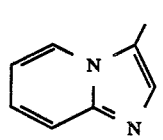 | 156 | 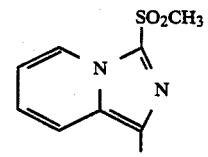 | 218–220 |
| 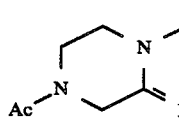 | 226 | 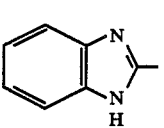 | 243 |

TABLE I-continued
R—CO—NH—NH₂  (II)
| R | M.p. (°C.) | R | M.p. (°C.) |
|---|---|---|---|
| 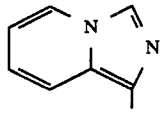 | 189 | 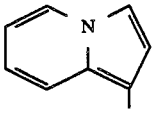 | 130 |
| 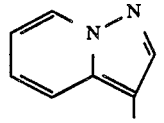 | 195 | 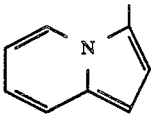 | 172 |
TABLE II
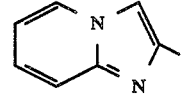  (I)
| Compound | R | n | M.p. (°C.) |
|---|---|---|---|
| 1 | 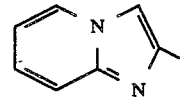 | 0 | 280 |
| 2 | 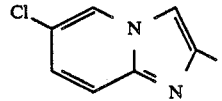 | 1 | 310 |
| 3 | 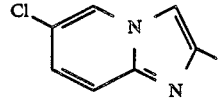 | 0 | 316 |
| 4 | 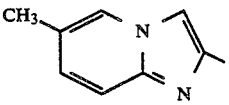 | 1 | 318 |
| 5 | 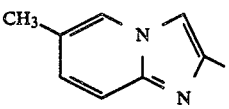 | 0 | 282 |
| 6 | 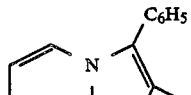 | 1 | 302 |
| 7 | 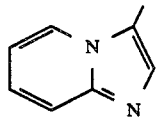 | 0 | 245 |
| 8 | 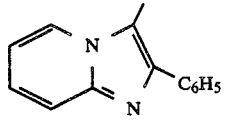 | 0 | 260 |
| 9 | 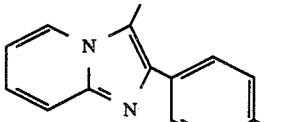 | 0 | 218 |
| 10 | 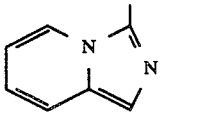 | 0 | 244–245 |
| 11 | 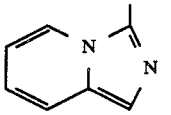 | 0 | 300 |
| 12 | 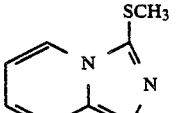 | 1 | 255–256 |
| 13 | 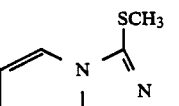 | 0 | 258 |
| 14 | 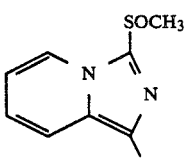 | 1 | 250 |
| 15 | SOCH₃ | 0 | 294 |

TABLE II-continued

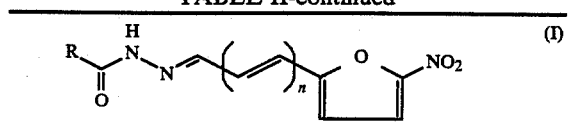

| Compound | R | n | M.p. (°C.) |
|---|---|---|---|
| 16 | (imidazo[1,5-a]pyridine with SO2CH3 and CH3) | 0 | 305–306 |
| 17 | (imidazo[1,5-a]pyridine with CH3) | 0 | 300 |
| 18 | (pyrazolo[1,5-a]pyridine with CH3) | 0 | 264 |
| 19 | (pyrazolo[1,5-a]pyridine with CH3) | 1 | 250 |
| 20 | (indolizine with CH3) | 0 | 236 |
| 21 | (indolizine with CH3) | 0 | 218 |
| 22 | (indolizine with CH3) | 1 | 211 |
| 23 | (tetrahydroindolizine with CH3) | 0 | 146 |
| 24 | (tetrahydroindolizine with CH3) | 0 | 242 |
| 25 | (tetrahydroindolizine with CH3) | 1 | 219 |

TABLE II-continued

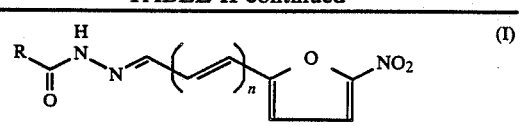

| Compound | R | n | M.p. (°C.) |
|---|---|---|---|
| 26 | (imidazo[1,2-a]pyrazine with CH3) | 0 | 329–330 |
| 27 | (imidazo-piperazine with CH3, HN) | 0 | 242 |
| 28 | (imidazo-piperazine with CH3, CH3CO-N) | 0 | 255 |
| 29 | (imidazo[2,1-b]thiazole with CH3) | 0 | 316 |
| 30 | (imidazo[2,1-b]thiazole with CH3) | 1 | 332 |
| 31 | (thieno[2,3-b]pyrrole with CH3) | 0 | 272 |
| 32 | (thieno[2,3-b]pyrrole with CH3) | 1 | 271 |
| 33 | (thieno[3,2-b]pyrrole with CH3) | 0 | 269 |
| 34 | (thieno[3,2-b]pyrrole with CH3) | 1 | 266 |
| 35 | (pyrido-pyrazinone with CH3) | 0 | 315 |

TABLE II-continued

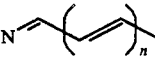

| Compound | R | n | M.p. (°C.) |
|---|---|---|---|
| 36 | (benzimidazol-2-yl) | 0 | 289 |

The compounds of the invention were subjected to pharmacological trials in the antibacterial, antiparasitic and antifungal field.

The compounds of the invention show an "in vitro" and "in vivo" inhibitory activity towards a large nubber of strains including, in particular, *Staphylococcus aureus, Escherichia coli, Mycobacterium ranae, Pseudomonas aeruginosa, Proteus vulgaris, Vibrio cholerae, Klebsiella pneumoniae,* Trichomonas, Salmonella, *Shighella flexneri, Candida albicans,* and this enables their use to be envisaged in various bacterial and parasitic infections, in particular those affecting the intestine.

The "in vitro" minimal inhibitory concentration, determined after dissolving the compounds in dimethylformamide (0.1%), varies according to the strain from 0.05 μg/ml to 20 μg/ml.

The studies carried out "in vivo" on experimental infection in mice demonstrate the oral activity of the compounds, since the latter inhibit the mortality induced by several strains of bacteria and produce complete sterilization of the digestive tract of the mouse.

The compounds show very low toxicity, which is generally very much greater than 1 g/kg.

The compounds of the invention can be used clinically in man at doses of from 20 mg to 1 g/day, the unit dosage being between 5 and 200 mg; the compounds can be used in animals at doses of from 1 to 20 mg/kg/day.

The compounds can be presented in any form suitable for oral, rectal or parenteral administration, for example in the form of capsules, tablets, granules, gelatin capsules or liquid solutions, syrups or suspensions to be taken by mouth, and can contain the appropriate excipients.

The compounds of the invention can be used in animals and man as antibacterials, intestinal antiseptics, antfungals and/or antiprotozoals. Acting at the intestinal level in man, they may be used for treating infectious functional colonopathies, diarrhoea caused by food or of other origin, enteritis, enterocolitis and bacillary dysentery.

The compounds of the invention may also be used for the protection and preservation of foodstuffs and to promote the growth of cattle by combating bacterial and parasitic infections.

We claim:

1. A nitrofuran derivative of the formula (I)

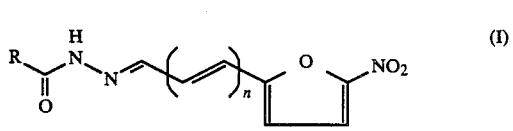

in which n is 0 or 1 and R is an imidazo[1,2-a]pyrid-2-yl, imidazo[2,1-b]thiazol-6-yl, imidazo[1,2-a]pyrazin-2-yl, 5,6,7,8-tetrahydroimidazo[1,2-a]pyrazin-2-yl, 7-acetyl-5,6,7,8-tetrahydroimidazo[1,2-a]pyrazin-2-yl, imidazo-[1,5-a]pyrid-1-yl, imidazo[1,5-a]pyrid-3-yl, pyrazolo-[1,5-a]pyrid-3-yl, 1-indolizinyl, 3-indolizinyl, 5,6,7,8-tetrahydro-1-indolizinyl, 5,6,7,8-tetrahydro-2-indolizinyl, 6H-thieno[2,3-b]pyrrol-5-yl, 4H-thieno[3,2-b]pyrrol-5-yl, 4-oxo-4H-pyrido[1,2-a]pyrimidin-3-yl, benzimidazol-2-yl or imidazo[1,2-a]pyrid-3-yl radical.

2. An antiparasitic composition which comprises, as active ingredient, an effective antiparasitic amount of a compound claimed in claim 1 in association with an excipient.

* * * * *